United States Patent [19]
Carter et al.

[11] Patent Number: 5,948,609
[45] Date of Patent: Sep. 7, 1999

[54] OXYGEN-TRANSPORTING ALBUMIN-BASED BLOOD REPLACEMENT COMPOSITION AND BLOOD VOLUME EXPANDER

[76] Inventors: Daniel C. Carter, 119 Wood Creek Dr.; Joseph X. Ho, 183 Water Oak Dr., both of Madison, Ala. 35758; Florian Ruker, Montigasse 6, A-1170 Vienna, Austria

[21] Appl. No.: 08/984,176

[22] Filed: Dec. 3, 1997

[51] Int. Cl.[6] .............................. C07K 14/76; C12N 5/00; A61K 38/38
[52] U.S. Cl. ............................. 435/1.2; 435/325; 514/12; 530/363; 530/362
[58] Field of Search .................................... 435/325, 69.1, 435/1.2, 1.1; 530/363, 362; 514/12

[56] References Cited

U.S. PATENT DOCUMENTS

| | | | |
|---|---|---|---|
| 5,480,866 | 1/1996 | Bonaventura et al. | 514/6 |
| 5,773,417 | 6/1998 | Bonaventura et al. | 514/21 |
| 5,780,594 | 7/1998 | Carter | 530/363 |

*Primary Examiner*—Robert A. Wax
*Assistant Examiner*—Bradley S. Mayhew
*Attorney, Agent, or Firm*—Larson & Taylor

[57] ABSTRACT

A recombinant serum albumin is provided which has been modified in the heme binding region so as to have the ability when bound to heme to be capable of reversibly binding oxygen. The modifications are directed to replacing at least one of several hydrophobic binding residues in the natural heme binding region with a hydrophilic residue such as histidine, or by inserting a histidine into these regions, and the resulting recombinant hemealbumin complex, or hemalbumin, is able to reversibly transport oxygen in a manner not possible using natural albumin. The resulting oxygen-transporting recombinant hemalbumin compositions of the invention can be utilized as safe and effective blood replacement compositions, or in other applications such as preservation of organs for transplantation which presently use serum albumin, and these compositions will be advantageous because they can function both as blood volume expanders and as oxygen transport systems at the same time.

20 Claims, 8 Drawing Sheets

SEQUENCE LISTING

<160> NUMBER OF SEQ ID NOS: 1

<210> SEQ ID NO 1
<211> LENGTH: 585
<212> TYPE: PRT
<213> ORGANISM: Homo sapiens

<400> SEQUENCE: 1

```
Asp Ala His Lys Ser Glu Val Ala His Arg Phe Lys Asp Leu Gly Glu
 1               5                  10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220
```

-continued

```
Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
            245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
            325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala His Asp Pro His Glu
            355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Lys Gln Leu Gly Glu
385                 390                 395                 400

Tyr Lys Phe Gln Asn Ala Leu Leu Val Arg Tyr Thr Lys Lys Val Pro
            405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
            450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
            485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
            565                 570                 575

Ala Ala Ser Gln Ala Ala Leu Gly Leu
            580                 585
```

OXYGEN-TRANSPORTING ALBUMIN-BASED BLOOD REPLACEMENT COMPOSITION AND BLOOD VOLUME EXPANDER

FIELD OF THE INVENTION

This invention relates in general to a recombinant albumin-based composition useful as both a blood substitute and blood volume expander, or in other applications wherein albumin-based solutions are employed, and in particular to a recombinant/genetically engineered serum albumin which has modifications in the heme binding regions so as to impart the ability of the heme-albumin complex to reversibly bind oxygen, and which can be utilized in compositions which can transport oxygen in the bloodstream.

BACKGROUND OF THE INVENTION

The serum albumins belong to a multigene family of proteins that includes alpha-fetoprotein and human group-specific component, also known as vitamin-D binding protein. The members of this multigene family are typically comprised of relatively large multi-domain proteins, and the serum albumins are the major soluble proteins of the circulatory system and contribute to many vital physiological processes. Serum albumin generally comprises about 50% of the total blood component by dry weight, and as such is responsible for roughly 80% of the maintenance of colloid osmotic blood pressure (see Peters, All About Albumin Biochemistry, Genetics, and Medical Applications, Academic Press, 1996) and is chiefly responsible for controlling the physiological pH of blood (see Figge et al., *Lab. Clin. Med.* 120:713–719, 1991).

The albumins and their related blood proteins also play an extremely important role in the transport, distribution and metabolism of many endogenous and exogenous ligands in the human body, including a variety of chemically diverse molecules including fatty acids, amino acids, steroids, calcium, metals such as copper and zinc, and various pharmaceutical agents. The albumin family of molecules are generally thought to facilitate transfer many of these ligands across organ-circulatory interfaces such as the liver, intestines, kidneys and the brain, and studies have suggested the existence of an albumin cell surface receptor. See, e.g., Schnitzer et al., *P.N.A.S.* 85:6773 (1988). The albumins are thus intimately involved in a wide range of circulatory and metabolic functions.

Human serum albumin (HSA) is a protein of about 66,500 kD protein and is comprised of 585 amino acids including at least 17 disulphide bridges. As with many of the members of the albumin family, human serum albumin plays an extremely important role in human physiology and is located in virtually every human tissue and bodily secretion. As indicated above, HSA has an outstanding ability to bind and transport and immense spectrum of ligands throughout the circulatory system including the long-chain fatty acids which are otherwise insoluble in circulating plasma. The atomic structure and particular details regarding the binding affinities of albumin and the specific regions primarily responsible for those binding properties have been previously determined as set forth in references such as He et al., *Nature* 358:209–215 (1992), Carter et al., *Eur. J. Biochem.* 226:1049–1052 (1994), Carter & Ho, "Structure of Serum Albumin", in *Advances in Protein Chemistry*, Volume 45, pages 153–203 (1994), and in co-pending U.S. patent application Ser. No. 08/448,196, filed May 25, 1993, now U.S. Pat. No. 5,780,594, incorporated herein by reference.

In addition to human serum albumin, studies have been made on albumins in a variety of animal species, and it has been determined that over 60% of the amino acid sequences are conserved among the known albumin sequences of many mammals such as bovine, rat and human serum albumin. Moreover, as more and more albumins from other animal species have been sequenced, it has been found that the albumins from a wide range of vertebrate species including sheep, frogs, salmon, mice, pigs and even sea lampreys share a relatively high structural homology, and all share the characteristic repeating pattern of disulphide bridges observed in human serum albumin. In short, all members of the albumin multigene family for which sequences have been determined have good internal sequence homology, thus suggesting that the proteins evolved from a common ancestral protein, and reflecting the vital nature and function of this protein. See, e.g., Carter & Ho, "Structure of Serum Albumin", 1994, referred to above.

Because of the vital role played by albumins, there are literally thousands of applications for serum albumin and its related proteins covering a wide range of physiological conditions, and most often, native serum albumin has been used. However, unlike blood proteins such as hemoglobin, native serum albumins are non-functional as oxygen transport systems, and thus have not been useful in blood replacement systems requiring oxygen transport. As set forth in the recent article by Tsuchida et al., *Bioconjugate Chem.* 8:534–538 (1997), although the formation of the complex between human serum albumin and hemin has been widely studied, the reduction of hemin to heme and the oxygenation of the heme bound to serum albumin has been difficult or impossible to achieve. For example, Bonaventura et al. (presentation at the 11th Congress of ISABI, Boston, Mass., 1994) preliminarily reported the reversible spectral change of HSA binding a heme derivative in the presence of a large molar excess of axial imidazole upon exposure to dioxin but did not succeed in obtaining a stable oxygen adduct.

In the field of blood replacement products, there are presently two separate and distinct categories of these products, namely those which deal primarily with $O_2$ transport, such as hemoglobin-based products, and those which are primarily utilized as volume expanders, including products that employ serum albumin. However, supplies with regard to both of these blood replacement products have been severely restricted over the past few years because of numerous concerns with regard to the safety of hemoglobin- and albumin-based products isolated from natural sources because of the concerns that the products will be infected with viral contaminants such as the AIDS virus, the hepatitis-B virus, or a number of other pathogenic microorganisms.

This problem is particularly amplified in the case of albumin since the principal source of this blood protein at present is through isolation from pooled outdated blood which only further increases the risk of infection from viral agents. As a result, the use of serum albumin has been somewhat limited despite the fact that it has been shown to be a very important additive in several different biological applications. For example, in addition to its use as a blood volume expander, albumin has been used as an additive to help preserve organs prior to transplantation. Further, albumin has also been used to promote growth in tissue cultures, and this ability is most likely associated with its role in transport of fatty acids. However, all of these applications are limited because of the inability of albumin to transport oxygen, and because of the problems associated with maintaining an adequate supply of safe and effective albumin.

In addition, even further restrictions on the supply of albumin have occurred because of the awareness of the potential problems of tainted blood, which has led to a steadily decreasing supply of individuals who are even willing to donate blood in the first place. The present awareness of AIDS and other transmittable diseases has caused many people to believe that intravenous blood withdrawal will give rise to the aforementioned disease conditions, and as a result, there has been a declining supply of safe and useful blood replacement products that might have otherwise been obtained from blood donations.

In light of these concerns with natural sources of blood proteins, recent attempts have been made to manufacture and market recombinant sources of blood proteins such as albumin. Currently, several manufacturers produce recombinant albumins, including Delta Biotechnologies, Ltd (see European Pat. App. 201,239), Green Cross Corporation of Japan (see Okabayashi et al., *J. Biochem.* 110:103–110, 1991), Vepex-Biotechnica, Ltd. of Hungary (see Kalman et al., Nucleic Acids Res. 18:6075–6081, 1990) and Rhone-Poulenc Rorer (see Fleer et al., *BioTechnology* 9:968–975, 1991). However, these attempts have suffered because the functionality of these blood products are often limited, and in particular there have not been any blood products which can safely and effectively achieve oxygen transport in the manner of the hemoglobin-based products and act as a useful blood volume expander at the same time in the manner of the albumin-based products. In addition, because the present albumin-based products that are available do not transport oxygen, there effectiveness in other applications, such as in organ preservation prior to transplantation, is also quite limited.

SUMMARY OF THE INVENTION

Accordingly, it is thus an object of the present invention to provide a novel blood replacement product which can be used both as an oxygen transport protein as well as a blood volume expander.

It is further an object of the present invention to provide a novel blood replacement product which can perform a variety of vital physiological functions, but which can be manufactured using recombinant blood proteins so as to provide a safe and effective blood product which eliminates the risk of contamination by harmful or deadly viruses and other animal contaminants.

It is still further an object of the present invention to provide a novel blood replacement product which utilizes a recombinant form of albumin which has been genetically modified so as to be capable of transporting oxygen in the circulatory system.

It is even further an object of the present invention to provide a novel blood replacement product which not only encompasses a variety of useful physiological functions including oxygen transport and expansion of blood volume, but which can be utilized in human and animal patients without affecting blood pH and without causing physiological disturbance.

It is still another object of the present invention to provide a novel albumin-based product which can reversibly transport oxygen so as to be useful in other applications such as the preservation of organs prior to transplantation and in the promotion of tissue culture growth in an enhanced manner.

These and other objects are achieved by virtue of the present invention which provides a recombinant blood replacement product comprising a serum albumin that has been genetically modified at the heme binding site so as to become capable of reversibly binding oxygen. These modifications are primarily directed towards the replacement of the key hydrophobic residues on either side of the protoporphyrin iron in the region of the albumin comprising the heme binding site with the hydrophilic residue histidine, or the insertion of histidine at these locations, which gives a recombinant hemalbumin having reversible oxygen-binding properties. As a result of the modifications in the heme binding region of the albumin, a recombinant oxygen-binding hemalbumin composition in accordance with the present invention is provided which can thus be utilized in blood replacement products that will act as an oxygen transport system as well as a blood volume expander.

In addition, because of the ability to reversibly bind oxygen, the compositions of the present invention will be useful in enhancing the usefulness of albumin in such applications as preservation of organs prior to transplantation and in supporting growth of tissue cultures. Furthermore, because the hemalbumin compositions of the present invention are prepared using recombinant means, they can be used safely and effectively in patients, or with organs or tissue cultures, without the risk of harmful or deadly contamination by viruses and other animal contaminants associated with blood products obtained from natural sources.

BRIEF DESCRIPTION OF THE DRAWINGS

The present invention will now be described in detail with respect to preferred embodiments thereof, which are to be taken together with the accompanying drawings, wherein.

DETAILED DESCRIPTION OF THE PREFERRED EMBODIMENTS

Figure 1:
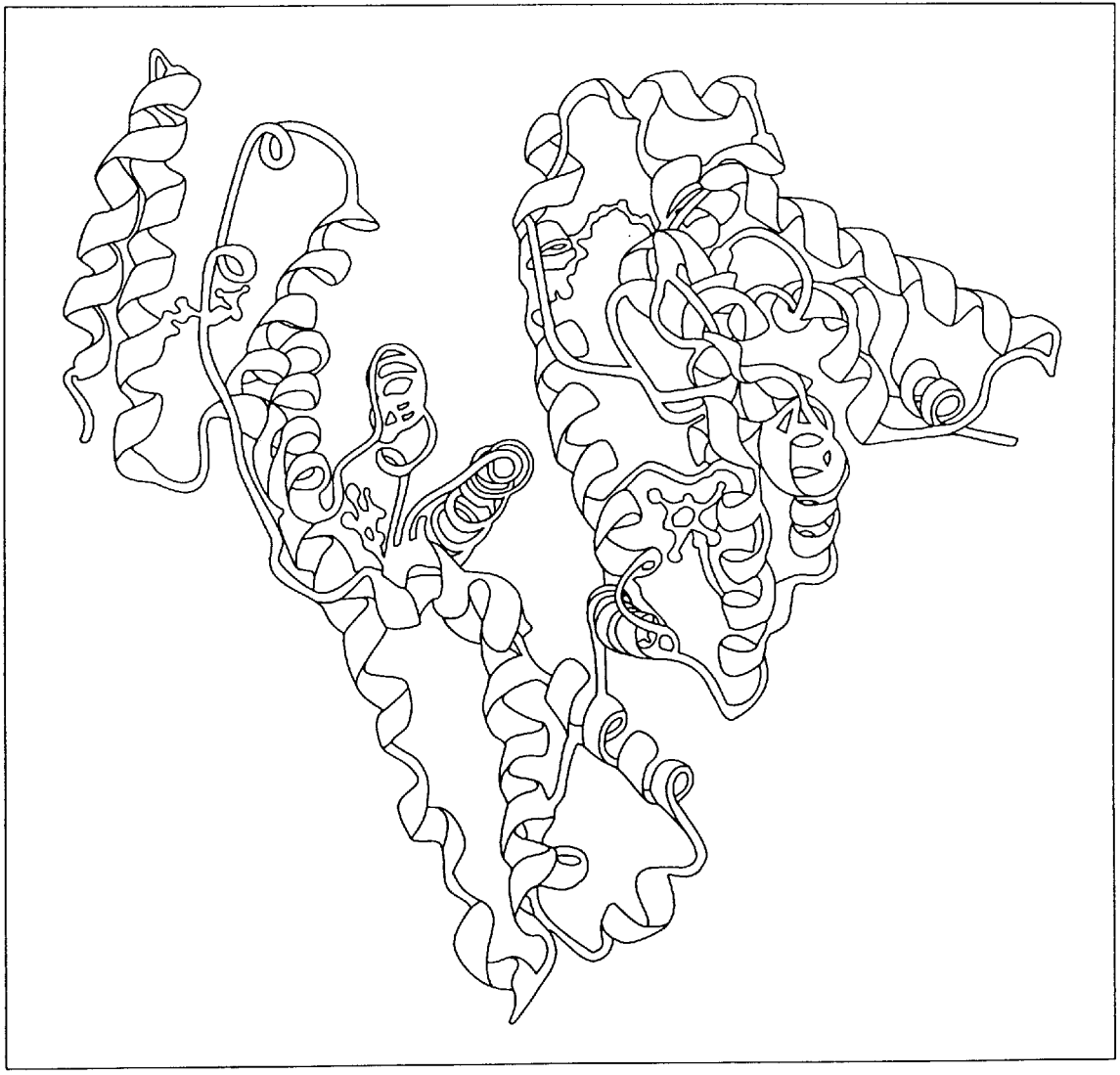
FIG. 1 is a view of the structure of human serum albumin illustrating the major binding regions as determined crystallographically.
Figure 2A:
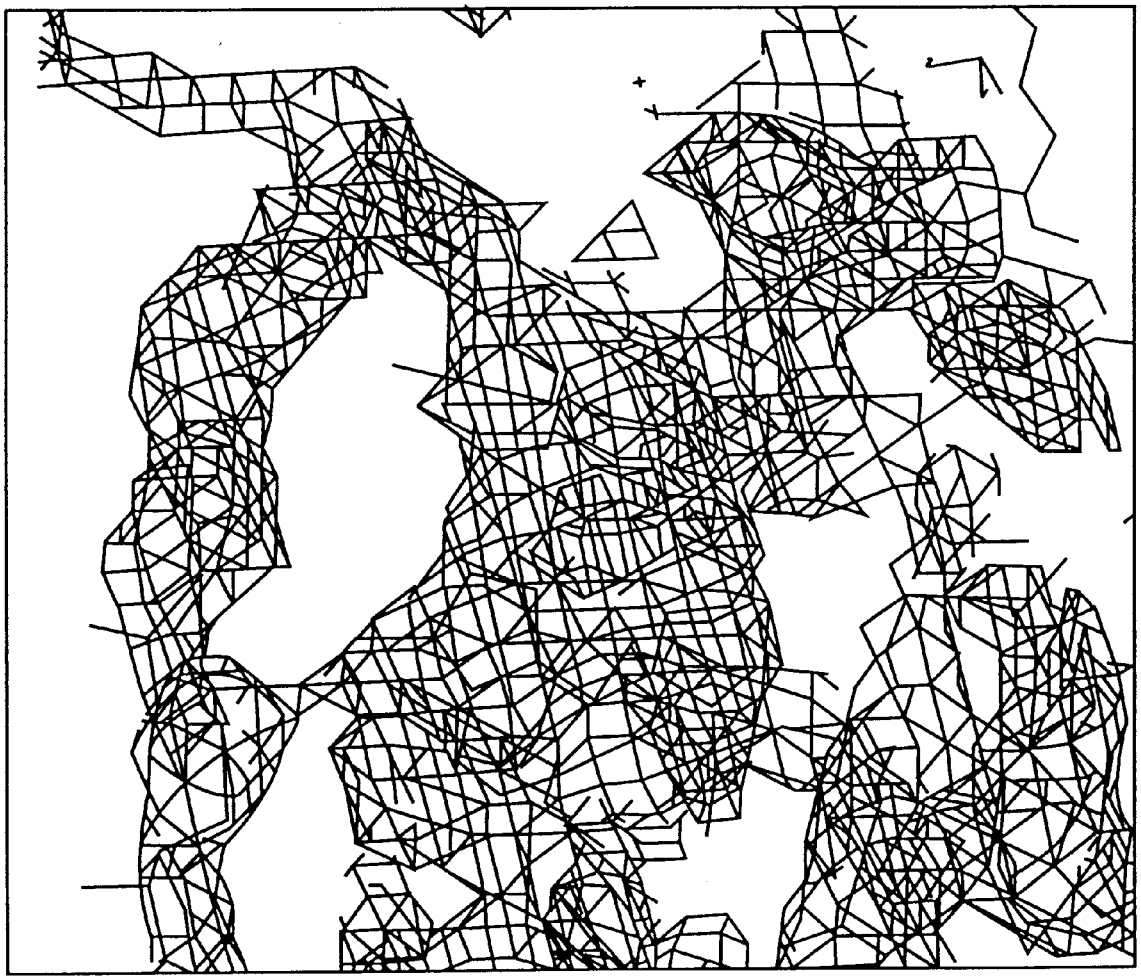
FIG. 2A is an electron density difference map revealing the binding location and chemistry of hemin to natural human serum albumin at 2.8 angstrom resolution.

In accordance with the present invention, a recombinant serum albumin is provided which is modified at the heme binding site so as to be capable of reversibly binding oxygen in the circulatory system and to be useful in compositions suitable as blood replacement products and in other applications. In the preferred embodiment, the blood replacement composition of the present invention is prepared by dissolving hemin and combining it with the recombinant serum albumin of the invention which has been modified in the manner detailed below, and although the invention is described specifically with regard to human serum albumin, it is contemplated that albumins from other species which have heme binding regions similar to that of human serum albumin will also be encompassed within the scope of the invention. Heme, or protoporphyrin, is one of the many metabolic products of endogenous origin and is produced from myoglobin and hemoglobin. In general, it appears that only the albumins from primates have a specialized high affinity site for protoporphyrin, and binding constants for this ligands are on the order of $1 \times 10^8$ Ka. Crystals of human serum albumin have been complexed with heme and studied using crystallographic means which have provided insights into the structure and specificity of the albumin binding regions, which are shown in FIG. 2A. These studies have provided means to investigate atomic interactions between albumin and heme and have allowed the determination of the precise heme binding site on the albumin molecule.

Figure 2B:
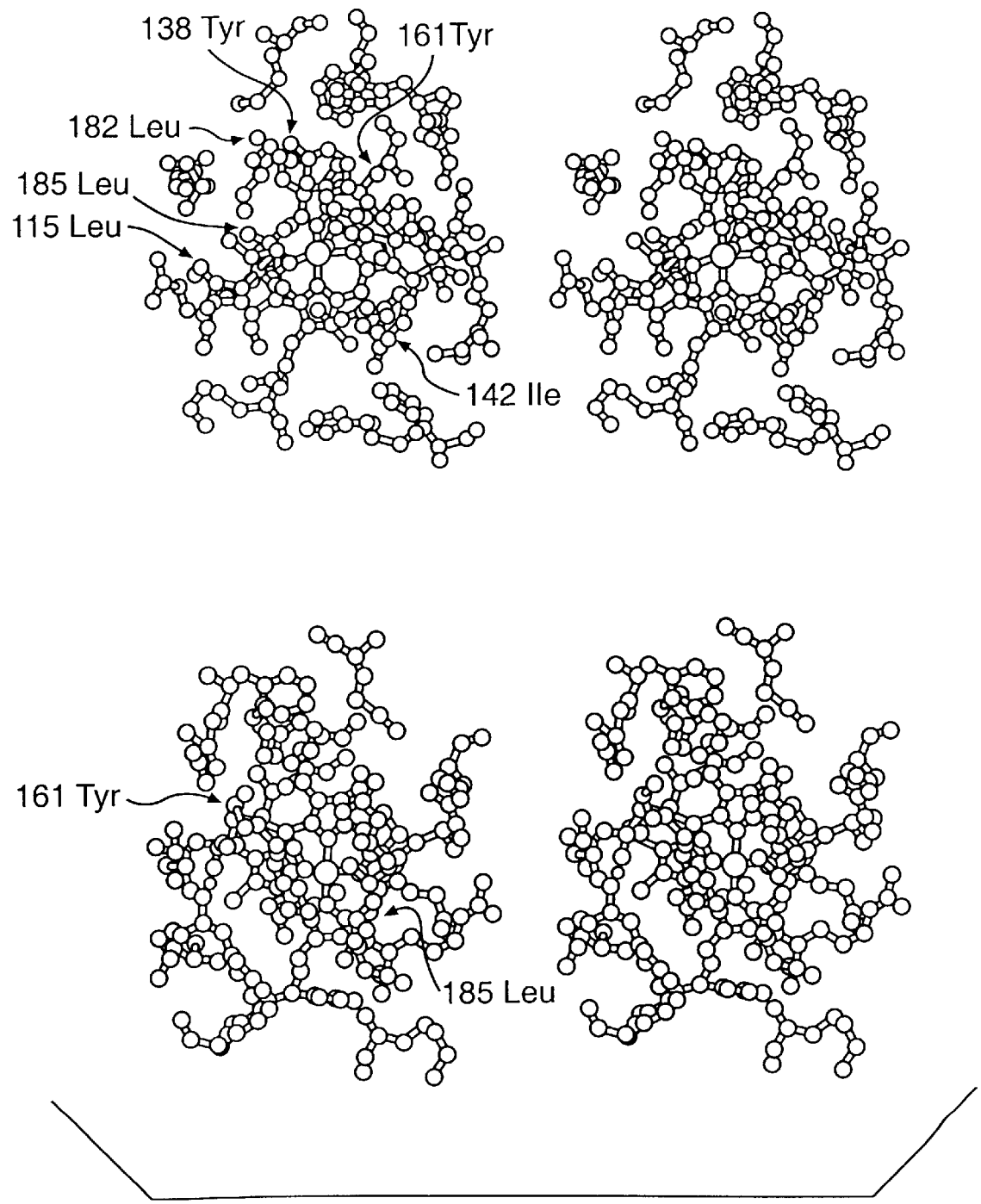
FIG. 2B is a stereo view of the atomic structure of the heme bound to subdomain IB of human serum albumin, with the front and back surfaces of the heme shown together with the labeled hydrophobic residues in close proximity.

In order to utilize crystallographic processes to study the binding between heme and albumin, hemin was dissolved and combined with human serum albumin in a 1:1 Molar ratio, which produces methemalbumin which is also crystallized utilizing conditions such as those disclosed in Carter et al., 1994 and co-pending U.S. patent application Ser. No. 08/448,196 now U.S. Pat. No. 5,780,594, incorporated herein by reference. X-ray diffraction data were collected and subsequent difference maps produced from these data revealed the binding location and chemistry of the heme, as observed in FIG. 2A. Moreover, through these studies, it was determined that the heme occupied a single binding site completely enclosed within subdomain IB of the albumin, as shown in FIG. 2B. It was also learned that the heme propionic acid residues are coordinated through salt bridges with arginine and lysine residues in a manner greatly similar to the chemistry of myoglobin and hemoglobin. However, unlike the structures of myoglobin and hemoglobin, in human serum albumin, the protoporphyrin iron is surrounded entirely by hydrophobic residues with no further chelation of the iron involved. Crystallographic studies have revealed that there are several key residues which appear to play an essential role in the formation of key heme coordination/interactions which are primarily responsible for imparting reversible oxygen binding, all of which are hydrophobic, and these residues appear to be situated at various locations surrounding the protoporphyrin iron. As a result, the hemalbumin produced by the binding of heme with natural serum albumin does not bind oxygen and thus cannot function as an oxygen transport system.

However, in accordance with the present invention, it has been determined that natural hemalbumin could be made into an oxygen-transporting molecule by modifying these key hydrophobic residues which surround the iron in the heme. In particular, in accordance with the present invention, the replacement of at least one of these key hydrophobic binding residues with a hydrophilic residue, such as histidine, will impart oxygen-binding properties in the hemalbumin so as to make this recombinant molecule useful as a oxygen-transporting blood replacement product.

In the preferred embodiment, at least one of the key hydrophobic residues on either side of the heme molecule is replaced with a hydrophilic residue such as histidine or other hydrophilic amino acid, and if so desired, additional key hydrophobic binding residues can be replaced with histidine. As would readily be understood by one of ordinary skill in this art, by "histidine" is meant the histidine amino acid in any form where its hydrophilic properties are retained, or any other histidine-like hydrophilic residue that has similar properties to histidine and would act in the same manner as histidine when employed in the present invention.

As determined by X-ray crystallographic studies, the key binding residues in serum albumin which bind heme are located within subdomain IB which is the region where the single binding site for heme is enclosed. In particular, as determined with regard to human serum albumin, there are key hydrophobic residues found on either side of the heme binding site. These key residues include a leucine (Lieu) at position 185 on the albumin protein and a tyrosine (Try) at position 161. On the other side of the heme binding site, key hydrophobic residues are located at the tyrosine (Tyr) at position 138 and the isoleucine (Ile) at position 142 on the albumin protein. In addition, leucine amino acid residues at positions 115, 139 and 182 also comprise key hydrophobic residues which when replaced by histidine will impart oxygen-binding properties when the recombinant albumin is used in a complex with heme.

In accordance with the present invention, the replacement of any one of these key binding hydrophobic residues with a hydrophilic amino acid residue such as histidine will be sufficient to impart reversible oxygen-binding properties to the hemalbumin and allow for the preparation of a variety of suitable blood products using this recombinant albumin. Preferably, the modified albumin of the present invention will have at least one key hydrophobic binding residue on either side of the heme binding site replaced with a hydrophilic residue such as histidine.

In addition, as one of ordinary skill in the art would readily understand, recombinant albumins in accordance with the invention may be obtained by insertion of a histidine in the amino acid chain at or near the location of the key binding residues referred to above. In this regard, another embodiment of the present invention is a recombinant albumin wherein at least one histidine is inserted at the location of a key hydrophobic binding site in the heme binding region, or at a position close enough to any of these key residues to provide the same effect on the albumin-heme binding as would the direct replacement of the hydrophobic residue at that location with histidine. In this embodiment, it is contemplated that an insertion of at least one histidine in any of the regions surrounding the key residues, namely the regions encompassed by amino acids at positions 111–119, the region at positions 134–146, the regions at positions 157–165, or the region at positions 178–189, will impart oxygen-transporting properties to the complex formed by heme combined with an albumin modified in this manner.

As would be readily understood by one of ordinary skill in this art, the substitution of the hydrophilic histidine residues for the hydrophobic residues of the natural albumin, or the insertion of histidine in the key hydrophobic binding regions, would be accomplished by any of a variety conventional means presently known to accomplish such recombination in the natural protein. In addition, as would also be recognized by those skilled in this art, the preparation of the recombinant albumin of the invention can be performed through the modification of nucleic acid coding for the albumin using any of the numerous conventional methods of recombination available to the skilled artisan.

In accordance with the present invention, it is contemplated that the modifications discussed herein will be useful when made to any natural serum albumin or to any of a variety of previously disclosed serum albumins that have small mutations which do not otherwise affect the properties of the albumins. As stated by Frank W. Putnam, as quoted in *All About Albumin Biochemistry, Genetics and Medical Applications*, referred to above, "unlike many other plasma proteins that exhibit polymorphisms and mutations, some of which are harmful, genetic variants of human albumin are rare and benign." Accordingly, when referring to "albumin" as used herein, it is contemplated that the present invention will include the normal albumin sequences and other mutations of the albumin that have been found to occur. As indicated above, the sequences of several of the albumin family of proteins have been disclosed in U.S. patent application Ser. No. 08/448,196, filed May 25, 1993, now U.S. Pat. No. 5,780,584 incorporated herein by reference.

In this regard, the sequence for human serum albumin and the genes that code for it are well known, and many researchers have published information in this regard, including okabayashi et al., *J. Biochem.* 110:103–110 (1991); Kalman et al., *Nucleic Acids Res.* 18:6075–6081 (1990); Fleer et al., *BioTechnology* 9:968–975 (1991); Minghetti et al., *J. Biol. Chem.* 261:6747–6757 (1986); and Hinchcliffe et al. in European Patent Application 201,239. Similarly, there are many well documented cases where specific mutations of the albumin protein were observed, such as the mutations that are reported in Peters, "All About Albumin Biochemistry, Genetics and Medical Applications" referred to above, at Table 4–8, pages 174–176. It is thus contemplated that these many forms of albumin will be suitable for modification in accordance with the present invention.

Figure 3:
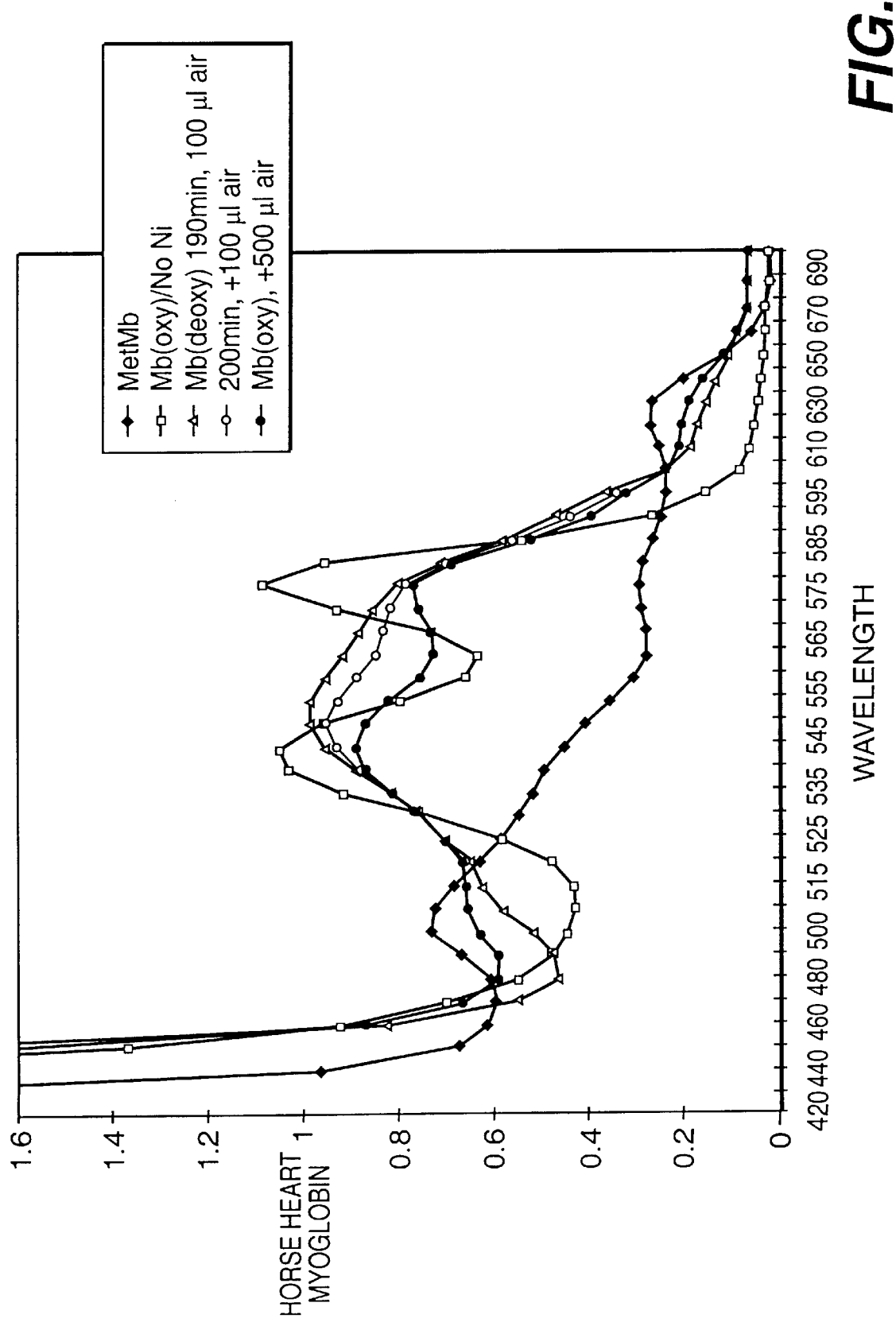
FIG. 3 is a graphic representation of the spectral characteristics of met-, oxy-, and deoxy- horse heart myoglobin.
Figure 4:
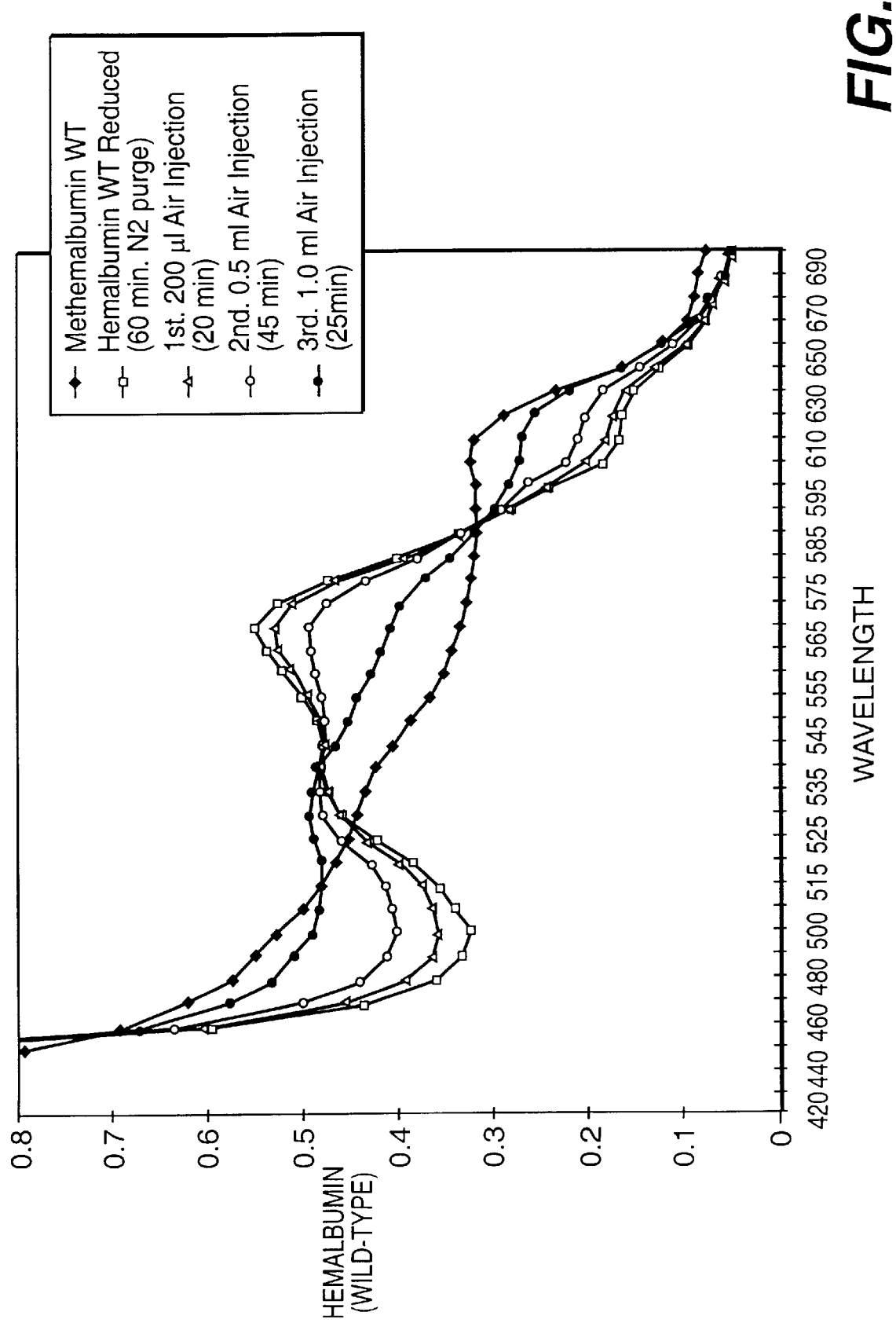
FIG. 4 is a graphic representation of the spectral characteristics of met-, oxy-, and deoxy- hemalbumin.

The modified albumins of the present invention have been tested with regard to their ability to bind oxygen, and these tests have confirmed that replacement of the key hydrophobic residues of the heme binding site with hydrophilic residues gives recombinant hemalbumins with oxygen binding properties. As observed in FIG. 3, experiments were conducted on horse heart myoglobin to indicate spectral changes reflecting shifting of myoglobin from the met form to the oxy and deoxy states of the reduced or active form of myoglobin. As indicated in FIG. 3, classic spectral changes are readily observable, and the reversibility of oxygen is readily demonstrated. Similar tests were conducted using wild-type methemalbumin as a control, and spectral patterns were obtained as indicated in FIG. 4. Here, consistent with the predicted chemistry of the complex as revealed by X-ray analysis, there is no oxygen binding detected by this method, and thus no reversibility, and the iron of the protoporphyrin is rapidly reoxidized.

Figure 5:
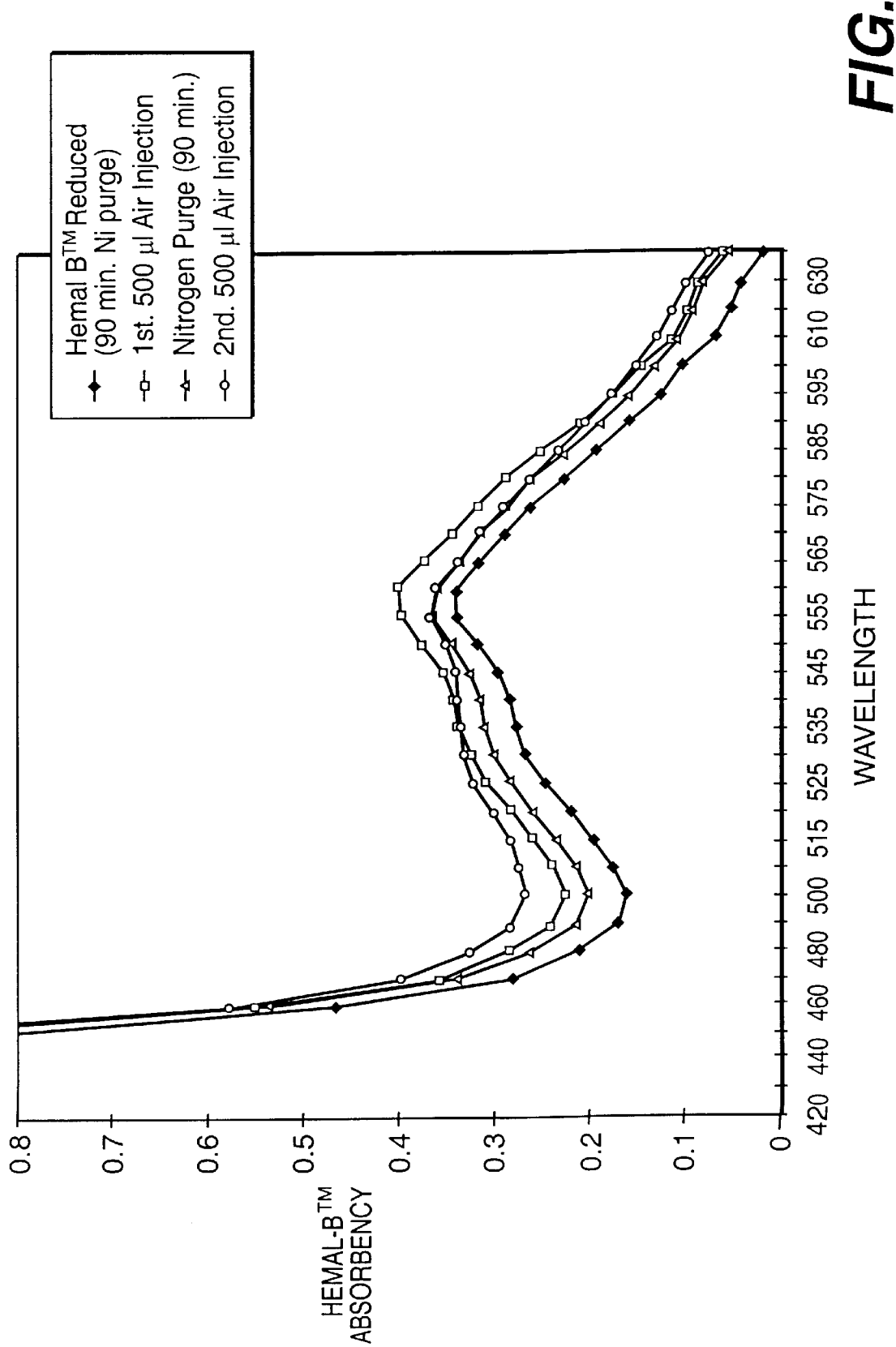
FIG. 5 is a graphic representation of the spectral characteristics of met-, oxy-, and deoxy- forms of a recombinant hemalbumin in accordance with the present invention.

In sharp contrast, using recombinant hemalbumin constructs in accordance with the present invention, pronounced and reversible spectral changes upon addition and subsequent removal of oxygen were observed which reflect that the constructs of the invention provide the hemalbumin with oxygen binding properties not present in wild-type hemalbumin. One such construct was a recombinant hemalbumin identified as r-hemalbumin B (or "Hemal B") in which at one side of the heme binding site, the tyrosine at position 161 was replaced by a histidine, and on the other side of the heme binding site, the isoleucine at position 142 was replaced with histidine. In tests conducted with regard to its properties upon introduction of oxygen, Hemal B exhibited a pronounced spectral change upon addition of oxygen which indicated that oxygen was being bound at the heme binding site of the recombinant albumin, as shown in the graph of FIG. 5. Furthermore, this spectral change was reversible when the tonometer was purged with nitrogen, thus indicating that the oxygen binding was reversible. The nature of the spectral reversibility indicated that a competitive process with reoxidation was occurring. In short, the susceptibility to reoxidation was dramatically improved from the wild-type hemalbumin, and was more in line with the values observed for myoglobin. This result is consistent with the more protected heme environment resulting from the incorporation of two histidines in accordance with the present invention.

Figure 7A:
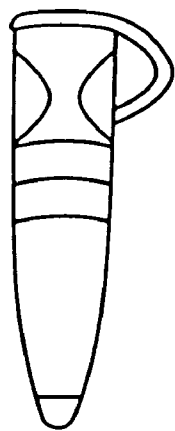
FIG. 7A shows the result of a microdialysis experiment illustrating the bound nature of hemin to a recombinant hemalbumin in accordance with the present invention.
Figure 7B:
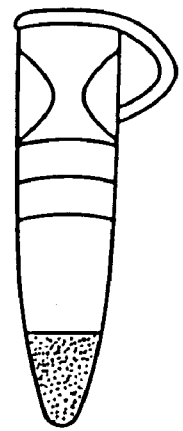
FIG. 7B shows the result of a microdialysis experiment illustrating that a hemin solution in the absence of the recombinant hemalbumin of the present invention passes freely through the size exclusion dialysis membrane.

Additional microdialysis experiments were conducted which confirmed that heme was bound to the recombinant hemalbumin of the present invention. As shown in FIG. 7A, where the hemin was bound to the recombinant hemalbumin of the present invention, this compound could not pass through an exclusion dialysis membrane, resulting in a clear eluant. As shown in FIG. 7B, however, a hemin solution in the absence of the recombinant albumin of the present invention freely passes through the size exclusion dialysis membrane, resulting in an eluant containing the hemin. These additional tests illustrated that heme was being bound to the recombinant hemalbumin of the present invention.

Figure 6:
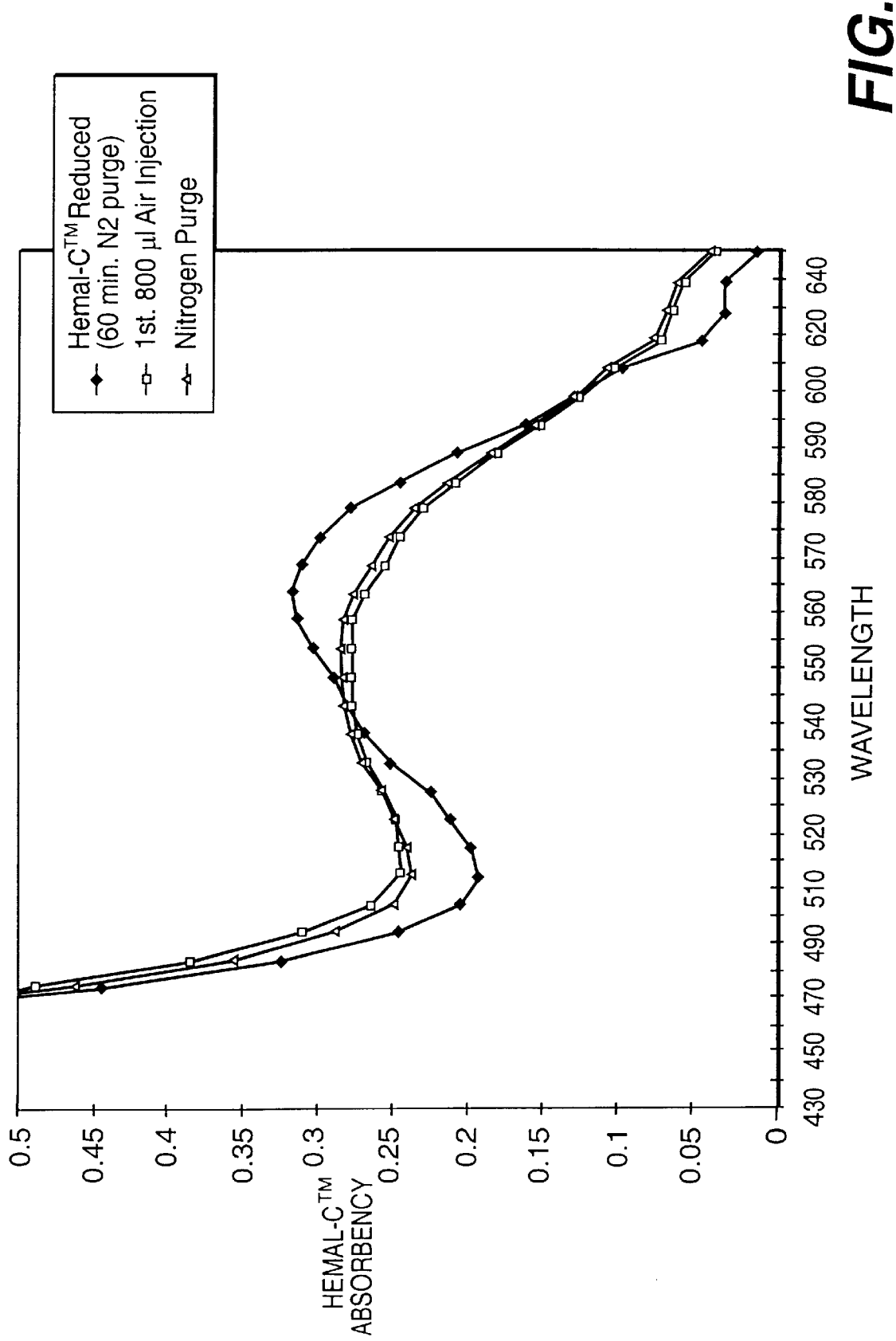
FIG. 6 is a graphic representation of the spectral characteristics of met-, oxy-, and deoxy- forms of an alternative recombinant hemalbumin in accordance with the present invention.

Still other forms of the recombinant hemalbumin of the present invention can be constructed which will have the ability to reversibly bind oxygen. For example, in another embodiment of the present invention, a recombinant albumin identified as r-hemalbumin C (or "Hemal C") wherein on one side of the heme binding site the leucine at position 185 was replaced with a histidine and on the other side of the heme binding site, the tyrosine at position 138 was replaced by histidine. As evidenced by the spectral analysis shown in FIG. 6, Hemal C also evidenced reversible oxygen binding in a manner not observed with wild-type hemalbumin. Accordingly, the genetically engineered albumins of the present invention have been shown to reversibly bind oxygen, and this has been accomplished in a simple and effective manner with only minor modifications of the parent albumin structure.

In accordance with the present invention, the recombinant hemalbumins of the invention which are capable of reversibly binding oxygen, and compositions containing these oxygen-transporting hemalbumins, can thus be used in a variety of applications dealing with blood products and blood substitutes. In addition, since the recombinant albumins of the present invention will have all of the properties of wild-type albumins, they can be used in other applications, including organ preservation and in tissue cultures, that albumins are currently used for. Thus, the modified albumins of the present invention can be prepared into appropriate blood products or substitute albumin products in conventional methods presently used for preparing such products.

Moreover, since the half-life of albumin in the circulatory system is approximately 19 days, the oxygen transport properties of products which use the hemalbumins of the present invention do not need to be as great as those found in natural blood products because the other protein-based oxygen transport products have half-lives of no more than a few hours. In fact, it has been noted that none of the blood replacement products currently on the market address problems such as chronic anemia (upwards of 3.2 million units needed per year) because those products do not function long enough in the body to be effective. See *Biocentury*, Sep. 3, 1997, pages 8–14. To the contrary, the recombinant hemalbumins of the present invention, once prepared using any of the conventional methods set forth above which would be apparent to one of ordinary skill in this art, can be made into compositions suitable for use as blood replacement products that will be useful both for the expansion of blood volume and/or for oxygen transport, and which have an extremely long useful life which increases their effectiveness for a wide variety of applications.

As would also be recognized by one skilled in the art, the recombinant hemalbumins of the present invention can be made into suitable blood replacement compositions in any of a variety of conventional methods well known in the art using physiologically acceptable fluids or other materials conventionally used in preparing other blood replacement products. Once prepared into physiologically compatible blood replacement solutions, the recombinant hemalbumins of the present invention can be administered as needed to increase blood volume or to enhance oxygen transport in the patient's circulatory system, for example, for patients who have suffered severe loss of blood, or during surgical operations.

As set forth above, the compositions which utilize the recombinant hemalbumins of the present invention are particularly advantageous as blood replacement products because they can be utilized both as a blood volume expander and an oxygen transporting medium, two distinct and separate functions which hereinbefore have not been found in a single product. Accordingly, blood products prepared using the hemalbumins of the present invention would comprise the first blood replacement product that could encompass both blood expansion and oxygen transport. In addition, because the recombinant hemalbumins of the present invention have only minor modifications from the wild-type form, they can be used in a safe and effective manner with little or no disturbance to the physiology of the patients. As one skilled in the art would realize, when using the recombinant albumins of the invention as a blood replacement product, blood pH can still be controlled as with conventional blood replacement, and transport of other small molecules such as pharmaceuticals would also remain intact. The blood products prepared using the recombinant albumins of the invention would thus comprise to first truly multifunctional blood replacement product which can act as a blood volume expander and yet reversibly bind oxygen, all in a safe and effective manner.

In addition, compositions utilizing the recombinant hemalbumins of the present invention will be useful in any other application which normally employs albumin-based products, such as in organ preservation and tissue cultures. For example, many albumin-based solutions are utilized in the preservation of organs prior to transplantation, but previously, such solutions were limited in usefulness and scope because they employed albumins which were not capable of oxygen transport. Through the use of the recombinant hemalbumins of the present invention, it will be possible to prepare enhanced solutions for use in organ preservation which because of their ability to reversibly bind oxygen will enhance the effectiveness and useful life of such a preservative solution. Similarly, the oxygen-transporting hemalbumin solutions of the present invention will also be useful as enhanced additives for promoting the growth of tissue cultures.

Even further, oxygen-transporting proteins such as the recombinant hemalbumins of the present invention will be useful in any application wherein the ability to reversibly bind oxygen will enhance the function of the albumin. For example, oxygen-transporting proteins that were incorporated into genetically engineered plants have been shown to markedly improve the growth and the fitness of a variety of plants. It thus will be possible to employ the modified albumins of the present invention to improve growth and production from those genetically engineered plants.

It is thus submitted that the foregoing embodiments are only illustrative of the claimed invention, and alternative embodiments well known or obvious to one skilled in the art not specifically set forth above also fall within the scope of the claims.

In addition, the following examples are presented as illustrative of the claimed invention, and are not deemed to be limiting of the scope of the invention, as defined by the claims appended hereto, in any manner.

EXAMPLE 1

In order to test the ability of the recombinant hemalbumin complexes of the present invention to bind oxygen, genetically engineered albumins were prepared using conventional recombination methods in yeast cultures. In one recombinant albumin produced in accordance with the invention ("Hemal B"), the tyrosine residue at position 161 was replaced with a histidine, and the isoleucine residue at position 142 was also replaced with a histidine. Oxygen binding experiments with Hemal B, and with horse heart myoglobin as a control, were conducted were conducted using a conventional modified tonometer, such as described in Allen et al., *J. Biol. Chem*/187:393–410 (1950) and Giardina et al., *Methods in Enzymol.*, 76:417–427 (1981). In these experiments, the albumin complex and the myoglobin were prepared using an equimolar concentration of heme, and the horse heart myoglobin was prepared at a concentration to give a $1.0 \times 10^{-7}$ M 3 ml solution.

In order to obtain the necessary spectral data reflecting reversible oxygen binding, a Pharmacia Biotech Ultrospec 2000 UV spectrophotometer was used. In the experimental runs, 3 ml of the protein solution being tested was placed in the tonometer and purged with nitrogen for several minutes. After the nitrogen purge is complete, base line readings are made using the spectrometer. The chamber is then sealed, and a sodium hydrosulphite reducing agent is added via syringe through a septum. The myoglobin was also reduced with Beta-Nicotinamide Adenine Dinucleotide (B-NADH). Following the reduction, the chamber is then purged for 30–60 minutes with nitrogen to remove any bound oxygen, and again a spectrum is recorded. The chamber is then sealed and precise amounts of air are added incrementally with a Hamilton gaslight syringe. After each addition, the solutions are mixed and allowed to equilibrate prior to additional spectral readings. In this manner, each of the graphs in FIGS. 3–5 were created.

As indicated in the graph shown in FIG. 3, the myoglobin system utilized as an example of an oxygen transporting protein demonstrated the classical spectral changes which evidenced reversible binding of oxygen. In prior experiments conducted with wild-type hemalbumin, as shown in FIG. 4, these classical spectral changes are absent, and no reversible oxygen binding is taking place. However, the above tests conducted with regard to Hemal B, as shown in the graph of FIG. 5, demonstrated the same classical spectral changes which clearly demonstrated that the recombinant albumin-heme complex of the present invention was capable of reversibly binding oxygen in a manner that was not possible using hemalbumin complexes incorporating only wild-type albumin.

EXAMPLE 2

As a second experiment to confirm that the heme was binding to the recombinant albumin of the present invention, microdialysis techniques were used on solutions of hemin with the recombinant albumins of the invention and on solutions of Hemin without added albumin. In these experiments, 10 microliters of a Hemin solution was prepared in dilute NaOH and added to a buffered solution of the recombinant hemalbumin identified as "Hemal B" to form a 1:1 molar protoporphyrin/albumin complex. In a second solution, 10 microliters of Hemin was added to an equivalent concentration in an identical buffer solution, but without the added albumin.

Using a Centripep™ microdialysis tube with a 20,000 molecular weight cutoff, the Hemin without the added recombinant albumin passed freely through the size exclusion membrane, as depicted in FIG. 7B. On the other hand, using the same 20,000 MW cutoff tube, microdialysis of the Hemin solution with the added recombinant albumin of the present invention produced a clear eluant as shown in FIG. 7A. This experiment confirmed the bound nature of the heme to the genetically modified albumins of the present invention.

EXAMPLE 3

Further experiments were conducted to determine if other embodiments of the present invention were capable of reversibly binding in the manner shown above for Hemal B. In these experiments, a second genetically engineered albumin was prepared using conventional recombination methods in yeast cultures, and in this case, one side of the heme binding site the leucine residue at position 185 was replaced with a histidine, and at the other side, the tyrosine residue at position 138 was also replaced with a histidine. This recombinant hemalbumin was identified as "Hemal C". Oxygen binding experiments with Hemal C were conducted in the same manner as described above for Hemal B in Example 1, and the resulting spectral data pattern that was obtained in shown in FIG. 6. As observed in the graph of FIG. 6, much as in the same manner as Hemal B and the horse heart myoglobin, Hemal C exhibited the classical spectral changes which demonstrated that other recombinant albumin-heme complexes in accordance with the present invention were also capable of reversibly binding oxygen in a manner not possible using hemalbumin with wild-type albumin.

What is claimed is:

1. A recombinant serum albumin having at least one hydrophobic binding residue of the subdomain 1B region replaced with a histidine, wherein the recombinant serum albumin binds heme to form a hemalbumin that reversibly binds oxygen.

2. A recombinant serum albumin according to claim 1 wherein the subdomain 1B region ranges from amino acid residues 111 to 189 in SEQ ID NO: 1.

3. A recombinant serum albumin according to claim 2 wherein the hydrophobic binding residue replaced with a histidine is selected from the group consisting of leucine at position 185, tyrosine at position 161, tyrosine at position 138, isoleucine at position 142, leucine at position 115, leucine at position 139, and leucine at position 182.

4. A recombinant serum albumin according to claim 1 wherein the tyrosine at position 161 is replaced with histidine and the isoleucine at position 142 is replaced with histidine.

5. A recombinant serum albumin according to claim 1 wherein the leucine at position 185 is replaced with histidine and the isoleucine at position 142 is replaced with histidine.

6. A recombinant serum albumin according to claim 1 wherein the tyrosine at position 161 is replaced with histidine and the tyrosine at position 138 is replaced with histidine.

7. A recombinant serum albumin according to claim 1 wherein the leucine at position 185 is replaced with histidine and the tyrosine at position 138 is replaced with histidine.

8. A recombinant hemalbumin composition comprising a recombinant serum albumin according to claim 1 bound to heme.

9. A blood replacement composition comprising a recombinant hemalbumin according to claim 8 in a physiologically acceptable blood replacement solution.

10. A recombinant serum albumin having at least one histidine inserted in subdomain IB, wherein the recombinant serum albumin binds heme to form a hemalbumin that reversibly binds oxygen.

11. A recombinant serum albumin according to claim 10 wherein the subdomain 1B region ranges from amino acid residues 111 to 189 in SEQ ID NO: 1.

12. A recombinant serum albumin according to claim 10 wherein at least one histidine is inserted in the serum albumin in the region encompassed by amino acids at positions 111–119.

13. A recombinant serum albumin according to claim 10 wherein at least one histidine is inserted in the serum albumin in the region encompassed by amino acids at positions 134–146.

14. A recombinant serum albumin according to claim 10 wherein at least one histidine is inserted in the serum albumin in the region encompassed by amino acids at positions 157–165.

15. A recombinant serum albumin according to claim 10 wherein at least one histidine is inserted in the serum albumin in the region encompassed by amino acids at positions 178–189.

16. A recombinant hemalbumin composition comprising a recombinant serum albumin according to claim 10 bound to heme.

17. A blood replacement composition comprising a recombinant hemalbumin according to claim 16 in a physiologically acceptable blood replacement solution.

18. A method of preserving tissues or organs prior to transplantation comprising isolating a tissue or organ suitable for transplantation and preserving the tissue or organ in a solution containing a recombinant serum albumin according to claim 1 bound to heme.

19. An improved tissue culture solution wherein the improvement comprises adding to the tissue culture solution a recombinant serum albumin according to claim 1 bound to heme.

20. A method of promoting the growth of tissue cultures comprising culturing tissues in a solution according to claim 19.

* * * * *